(12) United States Patent
Mautone

(10) Patent No.: US 6,645,467 B2
(45) Date of Patent: Nov. 11, 2003

(54) COMPOSITION AND METHOD FOR DECREASING UPPER RESPIRATORY AIRWAY RESISTANCE

(75) Inventor: Alan J. Mautone, Morristown, NJ (US)

(73) Assignee: Scientific Development and Research, Inc., Belleville, NJ (US)

( * ) Notice: Subject to any disclaimer, the term of this patent is extended or adjusted under 35 U.S.C. 154(b) by 0 days.

(21) Appl. No.: 10/011,994

(22) Filed: Dec. 4, 2001

(65) Prior Publication Data

US 2002/0090344 A1 Jul. 11, 2002

Related U.S. Application Data

(63) Continuation-in-part of application No. 09/639,739, filed on Aug. 16, 2000, which is a continuation-in-part of application No. 09/450,884, filed on Nov. 28, 1999, now Pat. No. 6,156,294.

(51) Int. Cl.$^7$ .......................... A61K 9/12; A61M 11/00; A61M 15/02
(52) U.S. Cl. ........................... 424/45; 424/46; 514/958; 514/975; 128/200.23
(58) Field of Search ..................... 424/45, 46; 514/958, 514/975; 128/200.23

(56) References Cited

U.S. PATENT DOCUMENTS 5,306,483 A * 4/1994 Mautone ..................... 424/45
6,156,294 A * 12/2000 Mautone ................ 128/200.23

OTHER PUBLICATIONS

U.S. patent application Ser. No. 09/639,739, Mautone, filed Aug. 16, 2000.*

* cited by examiner

*Primary Examiner*—Frederick Krass
*Assistant Examiner*—Donna Jagoe
(74) *Attorney, Agent, or Firm*—Richard L. Strauss, Esq.

(57) ABSTRACT

A composition, process and method is disclosed of decreasing mammalian upper respiratory system airway resistance by administering an aerosolized mixture of lipid crystals comprised of a mixture of one or more lipids surfactants and one or more spreading agents selected from the group consisting of sterols, lipids, fatty acids, cholesteryl esters, phospholipids, carbohydrates, and proteins, in powder form, and one or more propellants, in which the lipid surfactants and spreading agents are not soluble, through a mammalian external airway orifice. Upon administration, the propellant (s) are evaporated from the mixture and the lipid crystals are deposited upon the air/liquid interface resident upon the epithelial lining of the upper respiratory system forming an amorphous spread film thereupon substantially decreasing the resistance to air flow through said upper respiratory system. In a second preferred embodiment, a therapeutically active agent effective in the treatment of upper respiratory disease is added to the mixture of lipid crystals and upon administration of said aerosol mixture, the amorphous spread film formed thereby carries said therapeutically active agent throughout the tissues of the upper respiratory system. In an alternate preferred embodiment, the aforementioned reduction of surface tension and delivery of therapeutically active agents is provided by a mixture of lipid crystals comprised of surfactant(s), therapeutically active agents and a propellant in which such other components are not soluble.

133 Claims, No Drawings

COMPOSITION AND METHOD FOR DECREASING UPPER RESPIRATORY AIRWAY RESISTANCE

This is a continuation-in-part of U.S. patent application Ser. No. 09/639,739 filed Aug. 16, 2000 which, in turn, is a continuation-in-part of U.S. patent application Ser. No. 09/450,884 filed on Nov. 28, 1999 and which issued as U.S. Pat. No. 6,156,294 on Dec. 5, 2000.

FIELD OF INVENTION

The present invention relates to the field of pharmacological compositions and methods of utilizing such compositions in order to improve air flow throughout the upper respiratory system. More specifically, the present invention discloses compositions having powerful surfactant effect upon the air/liquid interface resident upon the epithelial lining of the upper respiratory system—and the use of such compounds—in order to open air spaces and air ways which have become partially or completely obstructed by proximal epithelial wall edema, constriction, adhesion and/or collapse caused by the presence and effect of highly viscous mucous exudate—generated as a product of inflammatory response—secreted thereupon.

BACKGROUND OF THE INVENTION

Pathological conditions can arise from, and can cause changes in surface tension values of air/liquid interfaces resident upon tissue surfaces, especially epithelial surface tissues, of and within various organs of mammalian anatomy. The naturally occurring "surfactant system" secreted upon the epithelial lining of the lung which is deficient in cases of R.D.S. is known to be comprised of a complex mixture of lipids, proteins and carbohydrates (as described in: Surfactants and the Lining of the Lung, The John Hopkinds University Press, Baltimore, 1988).

The prime function of the surfactant system is to stabilize the alveoli and associated small airways against collapse by decreasing the surface tension at the air/liquid interface. It is now believed that the action of the phospholipid component of the surfactant system is the principal source of the powerful surface tension reduction effect of the naturally occurring surfactant system of the lung. More specifically, it is known that the fully saturated diacylphospholipids, principally dipalmitoyl phosphatidylcholine (DPPC), provide liquid balance and anti-collapse properties to the lung's epithelial lining. In addition to DPPC, spreading agents, also found within the naturally occurring surfactant system, assist DPPC in rapidly forming a uniform spread film on the air/liquid surfaces of the lung. Such spreading agents include cholesteryl esters such as, for example, cholesteryl palmitate (CP); phospholipids such as, for example, diacylophosphatidylglycerols (PG), diacylphosphatidylethanolamines (PE), diacylphosphatidylserines (PS), diacylphosphatidylinositols (PI), sphingomelin (Sph) and Cardiolipin (Card) and virtually and other phospholipid, and the lysophospholipids; or any of the plasmalogens, dialklylphospholipids, phosphonolipids; carbohydrates and proteins, such as, for example, albumin, pulmonary surfactant proteins A, B, C and D. The naturally occurring surfactant system is further described in U.S. Pat. No. 5,306,483.

DPPC has been administered to infants with respiratory distress syndrome as a therapeutic measure in order to restore deficient or low levels of natural surfactant. For this purpose, DPPC has been administered by means of an aqueous aerosol generator (utilized with an incubator in which the infant resided during treatment). Endotracheal administration has also been utilized. DPPC therapy has been typified as utilizing natural surfactants (harvested from porcine or bovine lungs), or artificial, commercially synthesized compounds.

It has also heretofore been disclosed to utilize therapeutic agents, in combination with surfactant/spreading agents to effectively administer drug therapy uniformly throughout the epithelial lining of the lung. U.S. Pat. No. 5,306,483 (the "'483 patent") discloses a process to prepare lipid crystalline figures in fluorocarbon propellants for the delivery of therapeutically active substances which form amorphous fluids on delivery at the air/liquid interface of the lung and which can be utilized as an effective drug delivery system. More specifically, said patent discloses a process comprising (a) preparing a mixture of one or more lipid surfactants and one or more spreading agents, in powder form, a therapeutically active substance and one or more fluorocarbon propellants, said lipids, spreading agents and therapeutically active substances being insoluble in the propellants and said lipid surfactants and spreading agents being selected from cholesteryl esters, phospholipids, carbohydrates and proteins; and (b) evaporating the propellants from the mixture. The '483 patent teaches the combination of dipalmitoyl phosphatidylcholine (DPPC) or any of the other fully saturated Acyl chain phospholipids, 80.0 to 99.5% by weight, and other spreading agents, for example, phospholipids such as, but not limited to PG, PE, PS, PI, lysophospholipids, plasmalogens, dialkylphospholipids, diether phosphonolipids, Cardiolipin, sphingomyelin, 0.5 to 20.0% weight; neutral lipids like cholesteryl esters such as, but no limited to, cholesteryl palmitate, cholesteryl oleate, cholesteryl stearate, 0.5 to 10% by weight, carbohydrates, such as, but not limited to, glucose, fructose, galactose, pneumogalactan, dextrose, 0.5 to 10% by weight; and proteins such as, but not limited to albumin, pulmonary surfactant specific proteins A, B, C, and D 0.5 to 10% by weight, yielding lipid-crystalline structures in fluorocarbon (both chloro- and hydrofluorocarbon) propellants in which therapeutically active agents, drugs and other materials can be carried into the lungs after release from and through a metered dose nebulizer. The spreading agents referred to in the '483 patent are compounds such as the above-described phospholipids, lysophospholipids, plasmalogens, dialklyphospholipids, phosphonolipids, carbohydrates and proteins. The function of the spreading agent is to assist DPPC, or other phospholipids such as, for example, DPPG, in rapidly adsorbing and forming a spread film upon the air/liquid surfaces of the lungs. In addition, the '483 patent also discloses a process for preparing such lipid crystalline figures in fluorocarbon propellants without a therapeutically active substance for use as a tear (as for the eye).

The mammalian upper respiratory system is comprised of various conduits and chambers especially adapted for conduction of air to and away from the lungs. Besides forming a simple conduit, the upper respiratory system is responsible for warming, moisturizing, and removal, by means of entrapment and filtration, the various impurities found in inspired air so as to protect the lower respiratory system from disease and irritation, while simultaneously conditioning inspired air for maximum gas exchange. Generally, the upper respiratory system can be said to be comprised of the nose, nasal cavity, nasopharynx, paranasal sinuses, oropharynx and laryngopharynx.

As ambient air is inspired through the nose, it first passes through the external nares where relatively large hairs filter and remove larger particles from the air stream. From the external nares, the air is then drawn through the nasal cavity for further filtration. Within the nasal cavity, small boney protuberances known as the nasal conchae line the lateral walls of the chamber. The conchae, also known as turbinate bones, create great turbulence within the inspired air. The conchae thereby increase the collision and contact of smaller particulate matter with the adherent mucous coating of the epithelial surfaces lining the nasal cavity. Thus, such particles that avoid filtration by nasal hairs may become trapped within the nasal cavity. Mucous producing goblet cells which create the mucous coating of the upper respiratory system, assisted by the movement of cilia located on the free border of the epithelial cells, acts to continually flush such particulate matter, and any organisms which they may carry, towards the pharynx where they are swallowed and any such organisms destroyed in the acidic environment of the stomach. In addition, mucous production may also flush such matter out of the system through the external nares.

The paranasal sinuses also act as a filtration system in that the mucous membranes lining the sinuses also tend to trap impurities entering these structures during inspiration. Likewise, the nasopharynx, lined with respiratory epithelium, is also covered with mucoid secretions and capable of trapping and eliminating particulate contaminants in a similar manner.

As stated above, the upper respiratory system provides a conduit for the passage of air to the lungs. During normal physiologic function, the filtering structures and activities of the upper respiratory system do not interfere or present increased resistance to inspiration. However, during times of increased inflammatory activity, localized edema, or swelling of nasal and sinus membranes, can cause great resistance to normal respiration.

As discussed in greater detail below, inspired antigenic material can induce, through the inflammatory response, a marked increase in goblet cell mucous production. In addition, the inflammatory response quite often results in increased permeability of capillaries located close to the epithelial lining. Such increased permeability results in a localized edema or swelling of the epithelial lining of the upper respiratory system as various components of blood seep into the interstitial spaces. More specifically, such increased permeability allows the entry of white cells into the epithelial tissue where they may complex with the antigenic trigger of the inflammatory reaction resulting in phagocytosis, lysis, and enzymatic destruction of such foreign material. The localized edema—observed as substantial swelling of the epithelial lining of the upper respiratory system—tends to narrow the airways and airspaces. In addition, another common inflammatory response to antigenic challenge is the increased production of mucous and secretion of same upon the epithelial lining. The proteinaceous remnants of inflammatory phagocytosis, lysis and enzymatic destruction, discussed above, combines with the increased quantity of mucous to form an unusually viscous mucous coating upon the epithelial lining exhibiting higher levels of surface tension.

During the course of upper respiratory inflammation—characterized by the aforementioned edema and copious viscous mucous—opposing mucous laden epithelial surfaces lining the nasal cavity and sinuses—that ordinarily provide the above-described filtering functions—may become so swollen as to contact one another and so reduce airway volume. In addition, such swelling may be great enough, in the case of sections of the airway and airspaces demonstrating diminutive diameter, to allow proximal and/or opposing epithelial surfaces to come into direct continuous or intermittent contact. Upon such contact, the viscous mucoid exudate resident upon such surfaces may cause, due to the high surface tension properties discussed above, partial or complete closure of such air ways and air spaces.

For example, during the course of a common cold, bout of influenza, bacterial infection or allergy attack, antigenic proteins of such viruses, bacteria, and/or antigenic particles (for example, pollens, dust, dust mites, or other particulate antigenic material) present in inspired air may become trapped upon the normally present mucous coating of the lining epithelium whereupon the come into contact with macrophages. Such macrophages may induce an initial immune response by presenting such antigenic material to T-lymphocytes such as, for example, a CD4+ T lymphocyte. Upon such presentation, CD4+ lymphocytes respond, in part, by releasing a multitude of interleukins and cytokines which, in turn, promote the production of IgE. Mast cells, in close proximity with capillaries of the upper respiratory mucosa are induced by action of such IgE to secrete histamine. At the same time, histamine production increases both the volume of blood entering the tissue from local capillaries as well as increasing goblet cell production of mucous. In addition, presentation of antigen to lymphocyte leads to a cascade of inflammatory activity wherein pmns, with activated antibody, leach out of capillaries which have been made permeable thereto by histamine, into the respiratory epithelium wherein they complex with antigen for phagcytotic, lytic and macrophagic activities. The release of arachidonic acid from such activated mast cells, macrophages and pmns may lead to, for example, the production of luekotrienes. Luekotrienes, have inflammatory effects similar to histamine. However, luekotrienes effect such chemotaxis and enhanced mucous production to a far greater degree than histamine.

As discussed above, histamine and luekotrienes both act to vastly increase capillary permeability which, in turn, results in a general swelling of the mucosa as additional anti-body laden white blood cells leach out of said capillaries to form antibody-antigen complexes. Phagocytosis of such complexes by pmns, macrophages, and/or annihilation by means of the complement destruction cascade produces much waste material. This highly proteinaceous material, when added to the increased mucous secretions induced by these inflammatory pathways, forms copious amounts of viscous mucous resident upon said epithelial lining exhibiting substantially greater surface tension than that generated by the air/liquid interface of the epithelial lining in the absence of inflammation.

Two inflammatory effects, localized edema and increased exudate surface tension act, in concert, to promote and enable the above-described attraction and adhesion of proximal epithelial surfaces to one another leading to increased air way and air space resistance. However, it is the high surface tension properties of the mucoid secretions that allow and promote proximal inflamed tissues to remain adherent upon each other. In the absence of such increased surface tension, edema alone would, in many instances, only result in intermittent contact of proximal surfaces of the epithelial lining.

It has been heretofore possible to treat the underlying immune response with drugs effective in decreasing or eliminating same. For example, reduction of the production of mucous secretions is well known through the use of both anti-histamines and antiluekotreines. Indeed, such drug therapy may be effective in opening portions of the upper respiratory system closed by the combination of edema and increased mucous production discussed above. However, the use of anti-histamines may have undesired side effects such as, for example, drowsiness as they are often systemic in effect. Certain medications effective at reducing mucous production and inflammation such as, for example, pseudoephedrine, may cause nervousness, dry mouth, and other effects. Generally, undesirable side effects of such antihistamine type medications are dose dependent with greater dosage—required in some instances to effectively reduce viscous mucous production, and decrease edema—leading to an increase in such side and adverse effects. In addition, although mucous production may be annoying and uncomfortable, increased production of mucous and increased activity of the muco-ciliary transport system during the course of an upper respiratory infection serves the important function of flushing out bacteria while simultaneously preventing infection spread to the lung. Therefore, a drastic decrease or elimination of mucous production during the course of upper respiratory inflammatory episodes is not necessarily a desirable mode of treatment.

What is needed is a composition and method of delivering same which is effective in lowering the surface tension of the increased viscous mucous produced during inflammation of the upper respiratory system without effecting the purging effect of the muco-ciliary system, but rather assisting said system in washing out by products of the inflammatory process from the upper respiratory system while promoting the opening of the air spaces and air ways within.

Although the above-described therapeutic agents useful in treating the disorders causative of upper respiratory inflammation may have undesirable side effects, such effects, systemic in nature, may be reduced by application of reduced amounts of such agents directly to the effected tissues of the upper respiratory system. Thus, such therapeutics, administered via nasal inhalation, may be utilized to place the maximum amount of agent on the target tissue while minimizing systemic exposure. However, it has heretofore not been possible to ensure that such medication, delivered via oral or nasal inhalation, was delivered and distributed upon and substantially throughout the epithelial surfaces of the upper respiratory system or delivered with a carrier capable of significantly reducing the above-described increased surface tension without the use of additional drugs. What is needed is a compound, process and method wherein a pharmaceutical carrier is provided capable of providing direct and thorough application of therapeutically active agents effective in the treatment of upper respiratory inflammation, as well as the disorders causative thereof, directly to the epithelial lining of the upper respiratory system, while, simultaneously, and independently of said agents, providing a decrease in upper respiratory air flow resistance therethrough by means of powerful surfactant effect.

SUMMARY OF THE INVENTION

Now, in accordance with the present invention, a method of increasing and enhancing air flow through the mammalian upper respiratory system is disclosed wherein high surface tension resulting from viscous fluids and exudate resident upon the epithelial lining of upper respiratory air ways and air spaces is substantially reduced so as to promote the opening of said air ways and air spaces for facilitation of respiration therethrough.

In a first preferred embodiment of the present invention, a compound and method is disclosed wherein an aerosolized mixture of lipid crystals, administered to a mammal via inhalation, provides an effective reduction of upper respiratory airway resistance. In addition, a process for preparing a medicament effective in providing such treatment is disclosed. In the first preferred embodiment of the present invention, a mixture of one or more lipid surfactants and one or more spreading agents selected from the group consisting of sterols, lipids, fatty acids, cholesteryl esters, phospholipids, carbohydrates, and proteins, all in powder form, and one or more propellant is prepared. The propellant is selected to be one in which the one or more lipids and one or more spreading agents are not soluble so as to enable, in part, the formation of the below-described lipid crystals. For example, fluorocarbon propellants may be advantageously selected. The lipids and the spreading agents are likewise advantageously selected to be insoluble in the propellants.

The lipid surfactants utilized in practicing the method of the present invention are selected to be present in an amount sufficient to effectively reduce the surface tension of the liquid/air interface of the epithelial lining of the upper respiratory system, while the spreading agents are present in an amount sufficient to effectively distribute the lipids upon said lining. The term, "effectively reduce surface tension" as utilized throughout this application and in the claims, refers to that weight percentage range of lipid surfactant which, when present in said mixture of lipid crystals, provides a clinically significant decrease in upper respiratory system airflow resistance. The term, "effectively distribute the lipids upon said surface" refers to that weight percentage range of spreading agent that is required in order to provide adequate spreading and distribution of the lipids upon the air/liquid interface so that the lipid surfactant forms an amorphous spread film thereupon enabling the afore-mentioned reduction in airflow resistance.

The above-described clinically significant decrease in upper respiratory airflow resistance resulting from decreased surface tension, formation of a spread film upon the epithelial lining of the upper respiratory system—and the resultant increased volume/decreased airway resistance thereof—is provided by a mixture comprised of from about 99.99 to about 30 weight percent lipid surfactant and from about 70 to about 0.01 spreading agent. Increased effectiveness is provided by a preferred mixture comprised of from about 99.99 to about 50 weight percent lipid surfactant and from about 50 to about 0.01 weight percent spreading agent, both based on total weight of the mixture. However, it is still further preferred that the lipid surfactants utilized in practicing the method of the present invention are present in an amount of about 80 to 99.5 percent by weight and the spreading agents are present in an amount of about 0.5 to about 20 percent by weight, both based upon the total weight of the mixture. Combination of the one or more lipids, one or more spreading agents and one or more propellants results in the formation of a mixture of lipid crystals described in more detail, below. More specifically, the mixture is advantageously bottled in, for example, a metered dose administration bottle. Upon release from the bottle, an aerosolized mixture of lipid crystals is delivered therefrom. The mixture may be administered from the bottle by means of a nasal or oral inhalation device.

Upon administration, the propellant(s) are evaporated from the mixture and the aerosolized lipid crystals are deposited upon the air/liquid interface resident upon the epithelial lining of the air ways and air spaces of the upper respiratory system whereupon said lipid crystals form an amorphous spread film thereupon so as to effectively decrease the surface tension thereof.

The lipid crystals deposited upon the epithelial surfaces lining the upper respiratory system is comprised of one or more lipids which are advantageously selected to demonstrate powerful surfactant activity. In addition, the spreading agent combined therewith provide effective distribution of the surfactant over and upon the air/liquid surface resident upon said lining so as to form an amorphous spread film. In turn, the decrease in surface tension afforded thereby tends to separate proximal epithelial lining adherent, one upon the other, so as to increase air way and air space volume and to decrease air flow resistance. In addition, said decrease in surface tension also minimizes and, in some instances, eliminates the collection of fluids within the airways and air spaces of the upper respiratory system which might otherwise also serve to occlude, or partially occlude such areas. Administration of the aerosolized lipid crystals through nasal or oral inhalation results in deposition of the crystals upon the mucosal surfaces of the upper respiratory system including the sinus passages and sinus airways. However it is preferred, for optimal distribution of the mixture, the utilize nasal inhalation.

In a second preferred embodiment of the present invention, a compound and method is disclosed providing administration of therapeutically active agents, effective in the treatment of upper respiratory pathology, directly to the epithelial lining of the upper respiratory system as well as a process for preparing a medicament for providing such treatment. The term, "upper respiratory pathology" as utilized within this specification and throughout the claims, refers to those inflammatory and congestive conditions effecting the upper respiratory system which, as described above and below, tend to restrict upper respiratory airways through i. an increase in the amount and viscosity of epithelial wall secretions, ii proximal wall swelling and approximation resulting in a decrease in airway volume; and the collection of fluids therewithin. The term also refers to those causative viral, bacterial and mycotic infections which produce such inflammation and congestion. The term "upper respiratory pathology" also refers to allergic responses to any antigen and/or toxin capable of eliciting the aforementioned inflammatory response.

The second preferred embodiment of the present invention provides both effective administration of therapeutically active agents effective in the treatment of the aforementioned upper respiratory pathology, as well as reduction in upper respiratory airway resistance. In practicing the second preferred embodiment of the present invention, a mixture of one or more lipid surfactants, one or more spreading agents, one or more therapeutically active agent(s), and one or more propellants in which said surfactants, spreading agents and therapeutically active agents are not soluble, is prepared. The one or more lipid surfactants and spreading agents are advantageously selected from the group consisting of sterols, lipids, fatty acids, cholesteryl esters, phospholipids, carbohydrates, and proteins, all being in powder form.

The lipid surfactants utilized in practicing the method of the second preferred embodiment of the present invention are selected to be present in an amount sufficient to effectively reduce the surface tension of the air/liquid interface of the epithelial lining of the upper respiratory system, while the spreading agents are present in an amount sufficient to effectively effective distribution of the mixture of lipids and therapeutic agent(s) upon said interface so as to form a spread film thereupon. Effective reduction of surface tension is evidenced, in part and as discussed below, in decreased upper respiratory airflow resistance (as a result of increased volume of the subject airways.) However, said therapeutic agents also act to decrease airway resistance by reducing and/or eliminating inflammation, or the causative agents thereof, that results in increased airway resistance.

The above described effective decrease in surface tension and effective distribution of the mixture of lipids in combination with therapeutic agents is provided by a mixture comprised of from about 99.99 to about 30 weight percent lipid surfactant and from about 70 to about 0.01 spreading agent. However, it is preferred, and increased effectiveness is provided by a mixture comprised of from about 99.99 to about 50 weight percent lipid surfactant and from about 50 to about 0.01 weight percent spreading agent, both based on total weight of the mixture. However, it is still further preferred that in practicing the method of the second embodiment of the present invention, the lipid surfactants are present in an amount of about 80 to 99.5 percent by weight and the spreading agents are present in an amount of about 0.5 to about 20 percent by weight, both based upon the total weight of said mixture. The mixture resulting from the combination of lipid(s), spreading agent(s) and therapeutically active agent and propellant forms, upon release from an administration device, an aerosolized mixture of lipid crystals which act as carriers for said therapeutically active agent. A metered dose of the mixture of lipid crystals is administered, via nasal or oral inhalation, into the upper respiratory system of a mammal in need of such treatment. However, it is preferred to administer the mixture through nasal inhalation. A suitable bottle equipped with a metered dose valve and nasal or oral administration adaptor is advantageously utilized for this purpose and, upon activation, releases an aerosolized mixture of lipid crystals for administration.

Upon administration of the aerosolized mixture of lipid crystals, the propellants, carry the lipid crystals in combination with therapeutically active agent(s) (effective in the treatment of upper respiratory inflammation/congestion as well the underlying causes thereof), directly to the epithelial lining of the upper respiratory system. The lipid crystals and therapeutically active agent(s) are then deposited upon an air/liquid interface resident upon the epithelial tissue lining of the upper respiratory system. Upon contact with the interface, the aerosolized mixture of lipid crystals forms an amorphous spread film thereupon so as to effectively carry said therapeutically active agent effective throughout the epithelial lining.

As stated in further detail below, the therapeutically active agent is advantageously selected to be effective in the treatment of upper respiratory inflammation and congestion as well as agents effective in the treatment of the underlying causes and causative agents leading to the above-described inflammatory responses. For example, such agents may be selected to be effective in the treatment of viral, mycotic or bacterial infections, (as well as combinations thereof) underlying and causative of said inflammatory reactions. Therefore, the second preferred method of the present invention provides a method of administering therapeutically active agents directly to the epithelial lining of the upper respiratory system wherein said therapeutically active agents provide effective treatment for the subject inflammatory condition such as, for example edema—as well as the underlying causes thereof—while, simultaneously, the surfactant(s) and spreading agent(s) acts to directly and effectively open the air ways and air spaces by decreasing the surface tension of the viscous mucous exudate thereupon.

The lipid crystals deposited upon the air/liquid interface of said epithelial surfaces lining the upper respiratory system and the air/liquid interface resident thereupon is comprised of one or more lipids which are advantageously selected to demonstrate powerful surfactant activity and to serve as a carrier for selected therapeutic agent(s). In addition, the spreading agent deposited therewith provides complete and thorough distribution of the surfactant and therapeutic agent (s) throughout the lining of the upper respiratory system resulting in substantial decreases in airway resistance.

Administration of the lipid crystals through nasal or oral inhalation results in effective deposition of said crystals upon the air/liquid interfaces resident upon the epithelial lining throughout the upper respiratory system. Such deposition effectively decreases the surface tension of said surfaces. In those instances where, as discussed above, the increased surface tension and proximal airway swelling associated with upper respiratory inflammation and congestion has caused partial obstruction of the upper respiratory tract, the surface tension lowering properties of the lipid crystals acts to promote separation of proximal walls resulting in increased airway volume and a decrease to air flow resistance. In those embodiments of the present invention wherein delivery of therapeutically active agents to the upper respiratory system is provided, said agents are selected to be effective in the treatment of both the inflammatory process as well as the disorder underlying and leading to an upper respiratory inflammation. It is contemplated that such disorders may be of a microbial, for example, a viral, protozoic, bacterial, fungal; or non-microbial, such as, for example, particulate or of a toxic/irritant chemical origin.

In some instances, more than one such agent may be carried by means of the lipid crystals to the upper respiratory mucosa. Such agents are contemplated to include antibiotics, antiviral agents, anti-inflammatory agents (steroid and non-steroid) anti-histamines, decongestants, gene therapy agents, such as, for example, nucleic acids as well as combinations thereof.

In a first alternate embodiment of the present invention, a compound, process and method is disclosed providing administration of therapeutically active agents, effective in the treatment of upper respiratory pathology, directly to the epithelial lining of the upper respiratory system as well as a process for preparing a medicament for providing such treatment. In practicing the method and process of the first alternate embodiment of the present invention, a mixture of one or more lipid surfactants, one or more therapeutically active agent(s), effective in the treatment of upper respiratory inflammation as well as the underlying cause thereof, and one or more propellants—in which said lipid surfactant and therapeutically active agents are not soluble—is prepared. The lipid surfactant is selected from the group consisting of sterols, lipids, fatty acids, cholesteryl esters, phospholipids, carbohydrates and proteins. The therapeutic agent may be selected from any of the afore or below-mentioned therapeutically active agents so as to provide desired therapeutic effects (regarding treatment of inflammatory conditions and the causative agents thereof). In such embodiments the mixture of lipids is comprised of a lipid surfactant and a therapeutic agent and the lipid surfactant and therapeutic agent are advantageously selected to be present in the same weight ratios as those described above and below in regards to those embodiments incorporating surfactant/spreading agent components—the therapeutic agent being present in the same respective weight percentage range as the spreading agent in such embodiments. For example, said mixture may be comprised of from about 99.99 to about 30 weight percent lipid surfactant and from about 70 to about 0.01 therapeutic agent and provide effective reduction in surface tension and delivery of the therapeutically effective agent. Increased effectiveness is provided by a preferred mixture comprised of from about 99.99 to about 50 weight percent lipid surfactant and from about 50 to about 0.01 weight percent therapeutically active, both based on total weight of the mixture. However, it is still further preferred said mixture may be comprised of from about 80 to about 99.5 weight percent lipid surfactant and from about 20 to about 0.5 weight percent therapeutically active agent, based upon total weight of said mixture.

In practicing certain embodiments of the first alternative embodiment, the therapeutically active agent may be selected from the group consisting of sterols, lipids, fatty acids, cholesteryl esters, phospholipids, carbohydrates and proteins. In such embodiments, the therapeutically active agent acts in accordance with its own pharmacologic function, as well as providing spreading agent function.

As described above, the therapeutic agent is selected to be present within the above-described weight ranges and in an amount sufficient to treat the afore-mentioned upper respiratory inflammatory condition and/or the causative agents thereof. The remainder of the mixture is comprised of one or more of the above-described lipid surfactants which act to reduce the surface tension of the liquid/air interface of the epithelial lining of thereof. Upon evaporation of the propellant, an aerosolized mixture of lipid crystals is formed.

Upon administration of the mixture of lipid crystals and therapeutic agent to the upper respiratory system via, for example, a metered dose bottle, the lipid crystal come into contact, and form an amorphous spread film upon the air/liquid interface resident upon the epithelial lining thereof. The surfactant spread film reduces the surface tension of the interface while simultaneously delivering the therapeutic active agents to the afore-mentioned target tissues.

The lipids utilized in practicing the method of the present invention may be advantageously selected to be phospholipids, neutral lipids or mixtures thereof. The phospholipids utilized may be further advantageously selected to be any phospholipid of the class known as phosphatidlycholine including any fully saturated diacyl phosphatidlycholine including 1,2 dipalmitoyl phosphatidylcholine (DPPC); a diacylphosphatidylglycerol; a diacylphosphatidylethanolamine; a diacylphosphatidylserine; a diacylphosphatidylinositol; sphingomyelin, Cardiolipin, lysophospholipid; a plasmalogen; a diether phosphonolipid; or a dialklyphospholipid.

The lipids utilized in practicing the method and process of the present invention may also be advantageously selected to be either plant or animal sterols. For example, cholesterol, cholecalciferol and ergosterol may be selected. In addition fatty acids, such as, for example, palmitic acid and oleic acid may also be selected.

The cholesteryl esters utilized in practicing the method of the present invention may be advantageously selected to be cholesteryl palmitate, cholesteryl oleate or cholesteryl stearate. Carbohydrates utilized in the present invention may be advantageously selected to be glucose, fructose, galactose, pneumogalactan, or dextrose. Proteins especially suited and advantageously selected for use in the present invention include albumin, pulmonary surfactant specific proteins A or B or C or D, their synthetic analogs, and mixtures thereof.

The propellants utilized in practicing the present invention may, in certain embodiments, be advantageously selected to be a fluorocarbon propellant such as, for example, chlorofluorocarbon propellants, hydrofluorocarbons or mixtures thereof. In addition, the present invention contemplates carbon dioxide as a suitable propellant. It is also contemplated that the present invention may incorporate and select any pharmaceutical grade, hypo-allergenic propellant in which the other components of the mixture are not soluble—the propellant, lipids, spreading agents and therapeutically active agents must be selected so none of the afore-mentioned surfactants, spreading agents or therapeutically active agents are soluble, and thus dissolved, within the propellant. The propellant is thus selected in order to enable the formation of the aerosolized mixture of lipid crystals, discussed below. The mixture is advantageously prepared to yield crystalline forms that demonstrate a particle size equal to or less than 16 microns in diameter. The diminutive nature of the crystalline particles is, as discussed in detail below, highly advantageous in enabling dispersion and application of the aerosolized mixture.

DETAILED DESCRIPTION OF THE INVENTION

Throughout this specification and claims, the phrase "therapeutically active agent" includes any substance which is capable of altering a biologic, physiologic and/or immunologic function, in nature or degree and includes those substances generally referred to pharmacologic agents and drugs, including nucleic acids utilized in gene therapy, in order to provide treatment of the symptoms or underlying causes of the subject inflammation; the term "fluorocarbons" includes the class of both chlorofluorocarbons and hydrofluorocarbons; the term lipids includes the class of phospholipids including, but not limited to PC, PG, PE, PI and Cardiolipin; and the phrase "spreading agent(s)" refer to and includes PG, PE, PS, PI, Sph., Card., lysophospholipids, plasmalogens, dialkylphospholipids, and all others in the class phospholipid as well as cholesteryl esters (like CP), proteins and carbohydrates.

Throughout this specification and claims, the phrase "spreading agent(s)" refers to compounds, as listed above, which assist the one or more lipid surfactants such as, for example, DPPC, in rapidly adsorbing and forming an amorphous spread film on air/liquid interfaces such as that found upon the epithelial lined surfaces of the upper respiratory system. In addition, the compounds referred to as "spreading agent(s)", together with the one or more lipid surfactants, are responsible for achieving and maintaining biophysical properties including, but not limited to, reduction of intermolecular attractive forces, surface tension, and the resultant attractive forces generated thereby, that tend to cause opposed surfaces, such as the proximal epithelial lined walls of the upper respiratory system, to adhere to each other.

A major lipid component utilized in practicing a preferred embodiment of the present invention is advantageously selected to be the phospholipid 1,2 dipalmitoyl, phosphatidylcholine (DPPC). DPPC is the most surface active of the phospholipids or any of the subclass of fully saturated acyl chain phospholipids. That is to say that DPPC, in combination with any spreading agent(s) disclosed herein, has a maximum effect in reducing surface tension at an air/liquid interface.

Another, minor lipid component that also acts as a spreading agent for the major component is advantageously selected to be diacylphosphatidylglycerol (PG). The number of carbon atoms in the acyl chains R and R', (see PG formula below) can vary between 8 and 22 and may or may not be fully saturated. DPPC and PG can be synthesized. However, since DPPC and PG are the main phospholipid constituents of cells, they are also readily extractable from such cells by non-polar solvents, i.e., chloroform, ether, acetone. DPPC's structural formula is:

$$CH_3(CH_2)_{14}\overset{O}{\overset{\|}{C}}-O-CH_2$$
$$CH_3(CH_2)_{14}\overset{\|}{\underset{O}{C}}-O-\overset{|}{\underset{H_2C-O-\overset{O}{\overset{\|}{P}}-O-CH_2CH_2N-(CH_3)_3}{CH}}$$

and PG's structural formula is:

$$CH_2-CH-CH_2-O-\overset{O}{\overset{\|}{P}}-O-CH_2-\overset{OH}{\underset{OH}{\overset{|}{C}}}-CH_2$$
$$\underset{R}{\overset{|}{O=C}} \quad \underset{R'}{\overset{|}{C=O}} \quad \overset{OH}{\underset{H}{|}}$$

Phospholipids such as DPPC and CP may be obtained commercially, in a highly purified form from Fluka Chemical Co. of Ronkonkoma, N.Y.; Sigma Chemical CO. of St. Louis Mo.; and Avanti Polar Lipids of Birmingham, Ala. and Primedica of Cambridge, Mass.

DPPC and PG are preferred component(s) advantageously utilized in the present inventions methods for administering therapeutically active agents to the upper respiratory system. DPPC and PG may be selected to be present in the composition over a fairly wide range of from 99.99 to about 30 weight percent DPPC and from about 70 to about 0.01 PG based upon total weight of the mixture. Increased effectiveness is provided by a preferred mixture comprised of from about 99.99 to about 50 weight percent DPPC and from about 50 to about 0.01 weight percent PG, both based on total weight of the mixture. However, it is still further preferred that weight percentages of from about 80% to about 99.5% DPPC and 20% to 0.5% PG be selected.

Throughout this disclosure and within the claims, the terms "reducing resistance to air flow," reducing airway resistance, "decreasing airway resistance" and "improving air flow" singly, in combination and interchangeably all refer to the reduction of the force required to enable inspiratory and expiratory airflow through the air spaces and airways of the upper respiratory system. The resistance referred to results from: reduction of the volume, partial obstruction, or complete occlusion of the upper respiratory airways and air spaces by swelling of the epithelium lining thereof; reduction of the volume, partial obstruction or complete obstruction of said air ways and air spaces by secretions resident upon said epithelial lining; and reduction of the volume, partial obstruction or complete obstruction of said airways and airspaces by fluids collecting therewithin resulting from the effects of an immune response. In those embodiments of the present invention wherein the aerosolized mixture of lipid crystals does not include, or act as a carrier for, a therapeutically active agent(s), the above-described reduction in resistance to air flow is brought about by the separation of proximal upper respiratory epithelial surfaces or elimination of fluid blockages by means of decreasing the surface tension thereupon. The term "proximal upper respiratory epithelial surfaces" as utilized throughout this specification and throughout the claims, refers to portions of the epithelial surface, lining the upper respiratory air ways and air spaces which, due to close proximity and/or opposition to each other, may come into contact as the result of, for example, epithelial or sub-epithelial edema, excess surface secretions, high surface tension, high negative air pressure or any combination thereof.

In those instances where the aerosolized mixture of lipid crystals does include and act as a carrier for a therapeutically active agent(s), the above-described reduction in resistance to air flow is brought about by: lowering the surface tension of proximal epithelial walls of and decreasing the pooling of secretions within said air ways and air spaces by means of said lipid crystals; and by reducing, eliminating or temporarily halting the inflammatory response causing the edema, and excess viscous secretions by i. direct anti-inflammatory effect, ii by treating the triggering factor of said inflammation, or iii. by combinations thereof.

For example, in those instances of the present invention wherein an anti-histamine is the therapeutically active agent, proximal walls of epithelial mucosa lined air ways of the upper respiratory system that are adherent to each other are separated and opened by means of both lipid surfactant mediated reduction of surface tension and, upon action of said anti-histamine, reduction of edema, reduction of mucous volume, and decrease in the viscous nature thereof.

Another lipid that can be utilized in practicing the methods of the present invention is cholesteryl palmitate(CP), which also serves as a spreading agent. This cholesteryl ester is a neutral lipid which belongs to a class of organic compounds that are also cell constituents and are extractable by non-polar solvents such as chloroform, methanol, ether, etc. The structural formula of CP is:

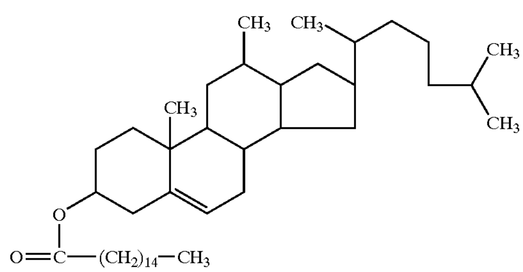

CP may be obtained commercially in a highly purified form from Fluka Chemical Co. and Sigma Chemical Co and Primedica. DPPC and CP may be selected to be present in the composition over a fairly wide range. The above-described surfactant and spreading agent effects, required to provided a decrease in upper respiratory airway resistance, are provided by a mixture comprised of from about 99.99 to about 30 weight percent DPPC and from about 70 to about 0.01 CP based upon total weight of the mixture. Increased effectiveness is provided by a preferred mixture comprised of from about 99.99 to about 50 weight percent DPPC and from about 50 to about 0.01 weight percent CP, both based on total weight of the mixture. However it is further preferred that the CP component be selected to be present in an amount ranging from about 0.5% to 20% by weight and DPPC be selected to be present from about 99.5% to about 80%, based upon the total weight of the mixture.

The term "therapeutically active agents effective in the treatment of upper respiratory inflammation" as utilized in and throughout this specification and claims, refers to those drugs effective in direct treatment of the inflammatory response causing the above-described air way and air space resistance as well as those drugs effective in the treatment of the underlying or precipitating cause of such inflammation such as, for example: treatment of infection, of microbial origin, such as, for example, viral, protozoic, bacterial, fungal and/or parasitic origin-; treatment of non-microbial allergic response resulting from antigenic matter such as, for instance, particulate (e.g. pollens and dust) and chemical triggers; as well as treatment of autoimmune disease causative of such inflammation. Therefore, it is contemplated that embodiments of the present invention may include as a therapeutic agent, singly or in combination: drugs effective in the direct treatment of the subject inflammation such as, for example, corticosteroids including, for example, betamethasone, including, for example, betamethasone dipropionate and betamethasone valerate as well as all other effective formulations; de-congestive agents such as phenylephrine, including, for example, phenylephrine HCL and phenylephrine bitartrate and all other effective formulations thereof; anti-viral agents such as, for example zovirax; and antibiotics including, for example erythromycin, amoxicillin, zythromax, and augmentin (amoxicillin and clavuliic acid) in all of their effective formulations. The term "all of their effective formulations" as used throughout this specification and in the claims refers to those specific species of a particular therapeutic agent effective in the treatment of the above-described upper respiratory disorders. It is also contemplated that said therapeutically effective agents include nucleic acids as well as the vectors thereof as utilized for gene therapy agents.

Such gene therapy agents, as the term is used herein, refers to a biochemical substance—as well as vectors thereof—selected from the group including, but not limited to, proteins, peptides or amino acids; nucleic acids such as DNA, including full length genes or fragments thereof derived from genomic, cDNA, or artificial coding sequences, gene regulatory elements, RNA including mRNA, tRNA, ribosomal RNA, ribozymes and anitsense RNA, oligonucleotides, oligoribonucleotides, deoxyribonucleotides and ribonucleotides as such agents may exist as isolated and purified compounds or in unpurified mixtures, such as tissue, cell or cell lysate. In addition, such agents may be naturally occurring, synthetic, or a mixture thereof.

The afore-mentioned therapeutically active agents acts to treat the pathology—allergic, infectious, inflammatory, toxic and combinations thereof—conditions that tends to occlude the upper air respiratory airways.

The combination of lipid component(s) and spreading agent component(s) disclosed herein, may be referred to, collectively, as the "carrier" when said combination is mixed with a therapeutically active agent so as to act as a carrier therefore. When practicing the method of the present invention wherein therapeutically active agents are administered directly to the epithelial lining of the upper respiratory system, it is preferred that carrier, the mixture of one or more lipids and one or more spreading agents, be comprised of a mixture of DPPC and CP in a 200:1 ratio (by weight). However, it has been found that a ratio range of from 5:1 to 300:1 (DPPC/CP) will also produce an effective carrier for this embodiment. If, for example, the therapeutic agent is selected to be betamethasone, the weight ratio of betamethasone to carrier (DPPC/CP) is advantageously selected to be 1 microgram betamethasone to 5 milligrams carrier. However, it has been found that a weight ratio range of 0.5 to 1000 micrograms betamethasone/5 milligrams carrier yields an effective and functional mixture.

When practicing the method of the present invention wherein the therapeutically active agent is selected to be phenylephrine it is preferred to select the weight ratio of phenylephrine to carrier to be 160 micrograms/995 milligrams. However, it has also been found that a weight ratio range of from 50 to 5000 micrograms (phenylephrine): 995 to 900 milligrams carrier, respectively, forms an effective mixture and functional mixture. The term "effective and functional mixture" as utilized throughout this application and in the claims refers to the effectiveness of the mixture of lipid crystals in combination with said therapeutically active agent resulting from the combinations disclosed herein in: (a) reaching the target tissue of the epithelium of the upper respiratory system; (b) reducing the surface tension thereupon; and (c) delivering an effective dose of therapeutic agent directly to and spreading upon and throughout the epithelial lining the upper respiratory tract so as to effectively bring symptomatic relief and/or resolution of the afore-mentioned pathological conditions underlying upper respiratory inflammation as well as acting, by means of said lipid crystals to open the air ways and air spaces by reduction of surface tension and elimination of pooled fluids.

When practicing the method of the present invention wherein the therapeutically active agent is selected to be the antibiotic erythromycin, the ratio of erythromycin to carrier is advantageously selected to be 200 mg antibiotic to 800 mg carrier (DPPC/CP) by weight. However, a weight range of from 50 to 200 mg erythromycin: from 950 to 800 mg carrier, respectively, has been found to be fully effective in practicing the present method.

Fluorocarbon propellants which may be advantageously utilized in practicing the method of the present invention comprise: trichlorodifluoromethane, dichlorodifluoromethane, and tetrafluoromethane or mixtures thereof, which are commercially available from Union Carbide Corp., Danbury, Conn. and Armstrong Laboratories, West Roxbury Mass. are advantageously selected for formation of the lipid crystalline figures of the present invention. Fluorocarbon propellants may be advantageously selected to be present over a range of 2 to 30 times the amount, by weight, of lipid, but components of lipid and fluorocarbon propellants both are needed in order to obtain the required lipid crystalline figures.

In practicing the methods of the present invention wherein therapeutically effective agents are administered directly to the epithelial tissue lining the upper respiratory tract, DPPC may be advantageously selected as the major lipid component since the amphoteric nature of this phospholipid allows the molecule to act as a carrier for any drug or therapeutic agent. However, the presence of a charge on other lipid components (a negative charge on PG, for example) would alter and further improve the carrying capacity of the lipid crystals for a particular therapeutic agent.

In addition to erythromycin and amoxicillin, the method of the present invention also contemplates selecting zythromax and Augmentin (amoxicillin+clavulinic acid) as antibiotic therapeutic agents and zovirax as an anti-viral agent. However, because of the highly amphoteric nature of the carrier utilized herein, the use of any presently known and available, as well as anti-viral, antibiotic or gene therapy developed in the future capable of providing effective treatment of infections of the upper respiratory tract are contemplated and fully functional with the methods and compositions herein.

EXAMPLE 1

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. All purchased materials were checked for purity by standard chromatographic analysis. The betamethasone utilized in this example was also purchased from Sigma Chemical. The DPPC and CP were then mixed in the dry powder form in a weight ratio of 200:1 (DPPC:CP). To 5 milligrams of the resultant carrier, 1 microgram of betamethasone was added in order to yield a weight ratio of 5000:1 (carrier: betamethasone). Then 5 grams of this mixture was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP:Betamethasone aerosolized mixture. However, metered dose valves having a greater dosing range are also contemplated and can be utilized in other embodiments of the present invention.

EXAMPLE II

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. The phenylephrine utilized in this example can also be purchased from Sigma Chem., St Louis, Mo. All purchased materials were checked for purity by standard chromatographic analysis. The DPPC and CP were then mixed in the dry powder form in a weight ratio of 200:1 (DPPC:CP). Thereafter, to 995 milligrams of the resultant carrier, 160 micrograms of phenylephrine was added so as to yield an approximate 6200:1 weight ratio of carrier to phenylephrine. Then 5 grams of the resultant mixture (DPPC/CP/phenylephrine) was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants and nasal administration adaptors. The bottles were immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP: phenylephrine aerosolized mixture. However, metered dose valves having a greater dosing range are also contemplated and can be advantageously utilized in practicing the methods of the present invention.

EXAMPLE III

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. The erythromycin utilized in this example can also be purchased from Sigma Chem., St Louis, Mo. All purchased materials were checked for purity by standard chromatographic analysis. The DPPC and CP were then mixed in the dry powder form in a weight ratio of 200:1 (DPPC:CP). Thereafter, to 800 milligrams of the resultant carrier, 200 milligrams of erythromycin was added so as to yield an approximate 4:1 weight ratio of carrier to erythromycin. Then 5 grams of the resultant mixture (DPPC/CP/erythromycin) was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants. The bottles were immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP: erythromycin aerosolized mixture. However, metered dose valves having a greater dosing range are also contemplated and can be advantageously utilized in practicing the methods of the present invention.

EXAMPLE IV

The aerosolized drug delivery system of the present invention was prepared from chromatographically pure (greater than 99%) DPPC, PG and CP. All of these materials were purchased from suppliers on the commercial market where they are available from several chemical supply houses. Specifically, the DPPC, CP and PG were purchased from Sigma Chem., St Louis, Mo. The erythromycin utilized in this example can also be purchased from Sigma Chem. All purchased materials were checked for purity by standard chromatographic analysis. The DPPC, PG and CP were then mixed in the dry powder form in a weight ratio of 7:1:0.35 (DPPC:PG:CP). Thereafter, to 800 milligrams of the resultant carrier, 200 milligrams of erythromycin was added so as to yield an approximate 4:1 weight ratio of carrier to erythromycin. Then 5 grams of this mixture was suspended in 55 grams of the first propellant, trichloromonofluoromethane (P11) and subdivided into 30 ml. Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal administration adapter. The suspension was homogenous. After standing at room temperature for about three days, a pellicle forms on top of the propellants but was easily resuspended by gentle shaking. The size of the metering valve can be varied to deliver from 1 mg up to 5.4 mg of the DPPC:PG:CP: erythromycin aerosolized mixture.

EXAMPLE V

Chromatographically pure DPPC and CP (99% pure) were obtained from Avanti Polar Lipids Co. of Birmingham, Ala. and Sigma Chemical Co. of St. Louis, Mo.

DPPC and CP were mixed in a weight ratio of 200:1 (DPPC:CP). Then 5 grams of this mixture was suspended in 55 grams of the first propellant, trichloromonofluoromethane (P11) and subdivided into 30 ml. Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal inhalation adapter. The suspension was homogenous. After standing at room temperature for about three days, a pellicle forms on top of the propellants but was easily re-suspended by gentle shaking. The size of the metering valve can be varied to deliver from 1 mg up to 5.4 mg of the DPPC:CP aerosolized mixture.

The afore-described Examples "I" through "IV" are specific embodiments of the aerosolized drug delivery system utilized in practicing the method of the present invention. Each of the afore-mentioned Examples "I" through "IV" may be administered by releasing a metered dose of the mixtures, by means of nasal or oral inhalation adaptor, through the nose or mouth. However, it is preferred to utilize a nasal adaptor and nasal inhalation. The aerosolized mixture, propelled by the above-described propellants, is then deposited uniformly throughout the epithelium of the upper respiratory system. When the crystalline lipid figures come in contact with the epithelial surface lining the upper respiratory system, an amorphous spread film layer forms upon the air/liquid interface resident thereupon. Upon such contact, said mixture of lipid crystals by means of the afore-mentioned surfactant properties, substantially lowers the surface tension of said air/liquid interface so as to allow the afore-mentioned opening of said air ways and air spaces and elimination of pooled liquid obstructions thereof.

In the above-described Example "I", wherein the therapeutically active agent is the anti-inflammatory, betamethasone, the agent acts directly upon the inflammatory process itself occurring within the upper respiratory epithelium, reducing the production of the afore-mentioned excess and viscous mucoid secretions while also decreasing tissue edema. Both excess mucoid secretions and edema act to reduce upper respiratory air flow since both of these factors tends to reduce air way and air way volume by reducing, partially obstructing, or totally occluding such air ways. Reduction in air way space likewise results in an increased effort necessary in order to move air through the upper respiratory system during inspiration and expiration. Thus, therapeutic agents of anti-inflammatory activity reduce air way and air space resistance by increasing conduit volume. However, in addition to such action of anti-inflammatory agents, the lipid surfactant spreading agent, such as, for example, DPPC and PG lipids, act independently of selected therapeutic agent(s) in promoting the opening of air ways and air spaces by reduction of the surface tension of the epithelial lining—by reducing the intermolecular and surface charges found at the air/interface of the viscous secretion covered lumen—. Thus, DPPC and/or DPPC/PG lipids of the present invention are able to open air ways and air spaces of the upper respiratory system independent of the action of therapeutic agents carried thereby.

The present invention also contemplates the use of antibiotics such as, for example, erythromycin (Example "III" and "IV"), amoxicillin, zythromax and augmentin (amoxicillin+clavulinic acid) as well an anti-viral agents. In such embodiments, the DPPC and/or DPPC/PG act to introduce such drugs in the upper respiratory epithelium in the same manner as described immediately above in regards to anti-inflammatory agents. Such anti-biotic and anti-viral agents act indirectly upon the inflammatory process provoked by the presence of antigenic microbial proteins by acting to reduce or eliminate the presence thereof. As the antigenic challenge of such microbes is reduced by the action of such therapeutic agents, the degree and intensity of inflammation—edema and excess viscous mucous—is reduced. However, while DPPC and DPPC/PG aerosolized mixtures act as carriers for such drugs, they also continue to provide the independent and more expeditiously effect on air way and air space resistance discussed above by effecting a substantial decrease in surface tension of the air/liquid interface resident upon the upper respiratory epithelium—on contact—. Therefore, in instances in which the method of the present invention is utilized to treat an underlying microbial infection of the upper respiratory system, direct application of antibiotic therapy to the target tissues is accomplished, leading to diminished microbial activity or death. Such anti-microbial effect indirectly reduces the increased air way and air space resistance of the upper respiratory system caused by inflammatory response thereto by reducing and/or eliminating the presence of such antigenic proteins.

In Example "V", above, preparation of an aerosolized mixture of lipid crystals for use in practicing the method of the present invention is disclosed that is advantageously formulated for decreasing upper respiratory air way and air space resistance without the use of a therapeutically active agent. In practicing the second preferred embodiment of the present invention, the aerosolized mixture, propelled by the above-described propellants, is deposited upon the air/liquid interface resident throughout the epithelial lining of the upper respiratory system. Upon contact of the crystalline lipid figures with the air/liquid interface, an amorphous spread film layer if formed thereupon, spreading throughout said air spaces and air ways. Upon contact with the air/liquid interface, the increased surface tensions thereof —associated with upper respiratory inflammation and discussed in great detail above—is substantially reduced. The reduction of said surface tension effects an opening of the air ways and air spaces of the upper respiratory system by releasing adherent or partially adherent proximal and/or opposing epithelial surfaces, lining said air ways and air spaces—from adhesion, one to another as well as reducing pooled fluids blocking or partially blocking said air spaces and air ways. In this example, no therapeutically active agent is included in the aerosolized mixture or contemplated in this embodiment. Increased air way and air space patency is provided by means of interaction of the surfactant/spreading agent combination alone. In many instances, especially in the absence of underlying infection embodiments of the present invention not incorporating therapeutically active agents may be preferred so as to control respiratory inflammation while minimizing systemic effects inherent in the use of many of such agents.

STRUCTURAL CHARACTERISTICS

Particle Size and Gross Configuration

Particle size of the nebulized crystals produced and utilized in practicing the present invention is, as discussed below, important for effective administration. The size (diameter) of the lipid crystals were therefore determined utilizing in a cascade impactor. Flow through the impactor was adjusted to be substantially identical to the flow from a nebulizer utilized in practicing the disclosed method. All of the lipid crystals were found to have a diameter equal to or less than 16 microns. The diameter of about 95 percent of the particles were found to be equal to or less than 4 microns in diameter. Of the particles found to be 4 microns or less, half were, in fact, 1 micron in diameter. The mean diameter demonstrated by the lipid crystals utilized in the method of the present invention was 1.75+/−0.25 microns.

Micronization may be advantageously utilized in order to insure reduced particle size. Therefore, the methods of the present invention also contemplate the use of a micronization mill such as, for example, the "DYNO" mill, type KDL, manufactured by Glen Mills Inc., of New Jersey in the preparation of the aerosolized mixture. For example, approximately 13.33 grams of CP and 83 g of DPPC powder were weighed and transferred to a bead mill within the milling chamber of a DYNO mill (having about 480 cc of glass beads). The chamber was then sealed. Thereafter, 1 liter of HFC-134a was added and the system chilled to about −100° C. at a pressure of approximately 65 psi. Milling was achieved in about 1 hour. Thereafter, the resultant slurry was utilized to fill 15 mil epoxy phenolic lined aluminum cans (Safet Embamet, St. Florantine, France), fitted with Valois metering valves (DFI/ACT/kematal, Valois, Le Neuborg, France with Micron-4 acuators (also Valois). A laser particle sizer, model 2600c, Malvern Instruments, Inc., was thereafter utilized to size the resultant particles as shown in Table "1", below. This data indicates that approximately 90% of the particles emitted fro the valve and actuator system are under 7 $\mu$m or less in diameter. The mean diameter (arithmetic mean) is approximately 5 $\mu$m and the mass median aerodynamic diameter (MMAD) is about 3.4 $\mu$m with a geometric standard deviation (GSD) of about 0.5. Particle size results in physically unstable dispersions should change dramatically over a few days of undisturbed storage.

TABLE 1

| | Particle Size Summary | | | | |
|---|---|---|---|---|---|
| Day Number | 90 Percentile | 50 Percentile | % ≦10 $\mu$m | MMAD | GSD |
| 1 | 6.9 $\mu$m | 5.1 $\mu$m | 100 | 3.4 | 0.5 |
| 2 | 6.8 $\mu$m | 4.8 $\mu$m | 99.9 | 3.5 | 0.5 |
| 3 | 7.3 $\mu$m | 5.4 $\mu$m | 100.0 | 3.5 | 0.5 |
| 4 | 6.5 $\mu$m | 4.6 $\mu$m | 99.9 | 3.2 | 0.5 |
| 5 | 6.8 $\mu$m | 4.7 $\mu$m | 100.0 | 3.4 | 0.5 |
| Mean | 6.9 ± 0.3 $\mu$m | 4.9 ± 0.3 $\mu$m | 100.0 | 3.4 ± 0.1 | 0.5 |

Structural characteristics of the mixture of lipid crystals utilized in practicing the present invention were further assessed by capturing the aerosolized particles on standard scanning electron microscopic grids fixed to glass slides at 22° C., (dry). The lipids deposited on glass both as dry particles and as coalesced droplets. The latter evaporated immediately leaving dry lipid. The dry lipids, were fixed in osmium vapor ($O_sO_4$), coated and viewed with a scanning electron microscope. Crystalline figures about 100 angstroms thick, were grouped in clumps on the dry surface. This is a unique configuration.

Crystalline Structure

The mixture of one or more lipids, one or more spreading and one or more propellants—in which said lipid surfactant and spreading agent are not soluble—disclosed in the present invention is especially formulated and combined to form a unique crystalline structure with physical dimensions highly advantageous to all embodiments. For example, the crystalline structure results in, as discussed above, a mean particle size of 1.75 microns. The minute physical dimensions of the individual nebulized particles enables the propellant utilized in practicing the present invention to easily and effectively transfer the disclosed mixture to and throughout the desired target tissue. A larger physical configurations such as, for example, a liposome, would not enable such diminutive particle size within and effective physical transport by the propellant.

FUNCTIONAL PROPERTIES

The aerosolized mixture of the present invention is crystalline. The crystalline nature of the mixture imparts increased efficiency of particle dispersion within the aerosol mist applied by means of a metered-dose nebulizer. For example, upon application, the fluorocarbon medium, either chlorofluorocarbon or hydrofluorocarbon, vaporizes rapidly and the DPPC/CP, DPPC/CP drug, DPPC/PG drug or DPPC/PG/CP drug dispersion deposits on an aqueous surface at 37° C., initially in the crystalline form, and then, instantaneously, spreads over the surface as an amorphous surface film. In embodiments wherein a therapeutic is combined with the carrier, the drug likewise is spread, upon and throughout the aqueous surface.

The surfactant/spreading agent functions and characteristics of the method and composition of the present invention were tested as follows. Aerosolized crystalline figures of the present invention were impacted upon a liquid surface (normal saline solution, NSS) at 37' C, 100% humidity in a surface balance resulted in a rapid spreading of a principally amorphous film that covered the entire surface (18.1 cm$^2$). Surface tension of the film was measured during expansion and compression at 37° C., 100% humidity. Film expansion to 110.4 cm$^2$ produced a surface tension of 72 dynes/cm and compression to 18.1 cm$^2$ lowered surface tension to less than 1 dyne/cm.

The terms and expressions which have been employed in the foregoing specification are used therein as terms of description and not limitation, and there is no intention, in the use of such terms and expressions, of excluding equivalents of the features shown and described or portions thereof, it being recognized that the scope of the invention is defined and limited only by the following claims.

I claim:

1. A method of reducing resistance to air flow through upper respiratory system airways of a mammal comprising administering a dose of a mixture of lipid crystals, as an aerosol, through an external airway of a mammal, said mixture being comprised of at least one lipid surfactant in an amount effective in lowering surface tension of an air/liquid interface resident upon epithelial tissue lining said upper respiratory system, at least one or more spreading agents in an amount effective in distributing said surfactant within said interface and at least one propellant in which said surfactants and spreading agents are not soluble, said surfactants and said spreading agents being selected from the group consisting of sterols, lipids, fatty acids, cholesteryl esters, phospholipids, carbohydrates, and proteins, all in powder form;

whereupon, when said mixture is so administered, said propellants are evaporated therefrom as said aerosolized mixture of lipid crystals come into contact with, and deposits upon the epithelial lining of the upper respiratory system and forms an amorphous spread film thereupon effectively reducing the surface tension thereof and thereby effecting a decrease in resistance to air flow therethrough.

2. The method of claim 1 wherein said amount of lipid surfactant is selected to be present in an amount of from about 99.99 to about 50 weight percent and wherein said spreading agent is selected to be present in an amount of from about 50 to about 0.01 weight percent.

3. The method of claim 1 wherein said lipid surfactant is selected to be present in an amount of from about 80 to about 99.5 weight percent and wherein said spreading agent is selected to be present in an amount of from about 20 to about 0.5 weight percent.

4. The method of claim 1 wherein a metered dose inhalation device is filled with said mixture of lipid crystals and thereafter said device is utilized to administer a metered dose of said mixture through an external nasal orifice of said mammal.

5. The method of claim 1 wherein a metered dose inhalation device is filled with said mixture of lipid crystals and thereafter said device is utilized to administer a metered dose of said mixture via oral inhalation.

6. The method of claim 1 wherein the sterols are selected from the group consisting of cholesterol, ergosterol, cholecalciferol and mixtures thereof.

7. The method of claim 1 wherein the fatty acids are selected from the group consisting of palmitic acid, oleic acid and mixtures thereof.

8. The method of claim 1 wherein the lipids are selected from the group consisting of phospholipds, neutral lipids and mixtures thereof.

9. The method of claim 8 wherein the phospholipids are any of a class known as phosphatidylcholines.

10. The method of claim 9 wherein the phosphatidylcholine is any fully saturated diacyl phosphatidylcholine.

11. The method of claim 10 wherein the fully saturated diacyl phosphatidylcholine is 1,2 dipalmitoyl phosphatidylcholine.

12. The method of claim 8 wherein the phospholipid is selected from the group consisting of a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphosphOlipid and mixtures thereof.

13. The method of claim 1 wherein the carbohydrates are selected from the group consisting of glucose, fructose, galactose, pneumogalactan, dextrose and mixtures thereof.

14. The method of claim 1 wherein the protein is selected from the group consisting of albumin and pulmonary surfactant specific proteins A, B, C, D and mixtures thereof.

15. The method of claim 1 wherein the cholesteryl ester is selected from the group consisting of cholesteryl palmitate, cholesteryl oleate, cholesteryl stearate and mixtures thereof.

16. The method of claim 1 wherein the propellants are fluorocarbons.

17. The method of claim 16 wherein the fluorocarbon is selected from the group consisting of a chlorofluorocarbon, hydrofluorocarbon and mixtures thereof.

18. The method of claim 1 wherein the propellant is carbon dioxide.

19. The method of claim 1 wherein the propellant is any pharmaceutical grade hyper-allergenic propellant in which neither the surfactant or spreading agent are soluble.

20. The method of claim 1 wherein 95 percent of said crystals demonstrate a particle size no greater than 4 microns in diameter.

21. A method of administering therapeutic agents, effective in the treatment of upper respiratory system pathology, directly to epithelial tissue lining said system while simultaneously decreasing resistance to airflow therethrough comprising administering a dose of a mixture of lipid crystals in combination with said therapeutic agents, as an aerosol, through an external airway of a mammal, said mixture being comprised of at least one lipid surfactants in an amount effective in lowering surface tension of an air/liquid interface resident upon epithelial tissue lining said upper respiratory system and at least one spreading agents in an amount effective in distributing said surfactants upon said interface, at least one therapeutically active agent effective in the treatment of upper respiratory pathology and at least one propellants, said surfactants and said spreading agents being selected from the group consisting of sterols, lipids, fatty acids, cholesteryl esters, phospholipids, carbohydrates, and proteins, said surfactants, spreading agents and therapeutically active agents all being in powder form and insoluble in the propellants, whereupon, when said mixture is so administered, said propellants evaporate from said mixture as said lipid crystals come into contact with, and deposit upon the epithelial lining of the upper respiratory system and form an amorphous spread film thereupon so as to effectively reduce the surface tension of said epithelial lining and thereby decrease resistance to airflow therethrough while simultaneously distributing said therapeutically active agent to said epithelial tissue.

22. The method of claim 21 wherein said lipid surfactant is selected to be present in an amount of from about 99.99 to about 50 weight percent and wherein said spreading agent is selected to be present in an amount of from about 50 to about 0.01 weight percent.

23. The method of claim 21 wherein said lipid surfactant is selected to be present in an amount of from about 80 to about 99.5 weight percent and wherein said spreading agent is selected to be present in an amount of from about 20 to about 0.5 weight percent.

24. The method of claim 21 wherein a metered dose inhalation device is filled with said mixture of lipid crystals in combination with said therapeutically active agent and thereafter said device is utilized to administer a metered dose of said mixture through an external nasal orifice of said mammal.

25. The method of claim 21 wherein a metered dose inhalation device is filled with said mixture of lipid crystals in combination with said therapeutically active agent and thereafter said device is utilized to administer a metered dose of said mixture by means of oral inhalation.

26. The method of claim 21 wherein the sterols are selected from the group consisting of cholesterol, ergosterol, cholecalciferol and mixtures thereof.

27. The method of claim 21 wherein the fatty acids are selected from the group consisting of palmitic acid, oleic acid and mixtures thereof.

28. The method of claim 21 wherein the lipids are selected from the group consisting of phospholipids, neutral lipids and mixtures thereof.

29. The method of claim 28 wherein the phospholipids are any of a class known as phosphatidylcholines.

30. The method of claim 29 wherein the phosphatidylcholine is any fully saturated diacyl phosphatidylcholine.

31. The method of claim 30 wherein the fully saturated diacyl phosphatidylcholine is 1,2 dipalmitoyl phosphatidylcholine.

32. The method of claim 28 wherein the phospholipid is selected from the group consisting of a diacylphosphatidylglycerol, diacylphosphatidylethanolamime, diacyiphosphatidylserifle, diacylphosphatidylinositol, sphingomelin, Cardiolipin, lysophospholipid, plasmalogen, diether phosphonolipid, dialkylphospholipid, and mixtures thereof.

33. The method of claim 21 wherein the carbohydrates are selected from the group consisting of glucose, fructose, galactose, pneumogalactan, dextrose and mixtures thereof.

34. The method of claim 21 wherein the protein is selected from the group consisting of albumin and pulmonary surfactant specific proteins A, B, C, D and mixtures thereof.

35. The method of claim 21 wherein the cholesteryl ester is selected from the group consisting of cholesteryl palmitate, cholesteryl oleate, cholesteryl stearate and mixtures thereof.

36. The method of claim 21 wherein said therapeutically active agent is selected from the group consisting of an anti-inflammatory, antibiotic, decongestant and gene therapy agent.

37. The method of claim 36 wherein said anti-inflammatory agent is betamethasone.

38. The method of claim 36 wherein said antibioitic is selected from the group consisting of erythromycin, amoxicillin, zythromax and Augmentin.

39. The method of claim 36 wherein said decongestant is phenylephrine.

40. The method of claim 21 wherein the propellants are fluorocarbons.

41. The method of claim 40 wherein the fluorocarbon is selected from the group consisting of a chlorofluorocarbon, hydrofluorocarbon and mixtures thereof.

42. The method of claim 21 wherein the propellant is carbon dioxide.

43. The method of claim 21 wherein the propellant is any pharmaceutical grade, hyper-allergenic propellant in which neither the surfactant, spreading agent or therapeutically active agent are soluble.

44. The method of claim 21 wherein 95 percent of said crystals demonstrate a particle size no greater than 4 microns in diameter.

45. A process for preparing an upper respiratory airway enhancing medicament comprising:

combining at least one lipid surfactant, at least one spreading agent and at least one propellant to form a mixture, said lipids and said spreading agents being selected from the group consisting of sterols, lipids, fatty acids, cholesteryl esters, phospholipids, carbohydrates, and proteins, all in powder form, wherein said lipids and said spreading agents are insoluble in the propellants and said lipid surfactants are selected to be present in an amount effective in reducing surface tension of an air/liquid interface resident upon epithelial tissue lining the upper respiratory system and said spreading agents are selected to be present in an amount effective in distributing said surfactant within said interface when said propellants are evaporated from said mixture to form a mixture of lipid crystals for use as the medicament.

46. The process of claim 45 wherein said lipid surfactant is selected to be present in an amount of from about 99.99 to about 50 weight percent and wherein said spreading agent is selected to be present in an amount of from about 50 to about 0.01 weight percent.

47. The process of claim 45 wherein said lipid surfactant is selected to be present in an amount of from about 80 to about 99.5 weight percent and wherein said spreading agent is selected to be present in an amount of from about 20 to about 0.5 weight percent.

48. The process of claim 45 further comprising bottling said mixture within a metered dose device.

49. The process of claim 45 wherein the sterols are selected from the group consisting of cholesterol, ergosterol, cholecalciferol and mixtures thereof.

50. The process of claim 45 wherein the fatty acids are selected from the group consisting of palmitic acid, oleic acid and mixtures thereof.

51. The process of claim 45 wherein the lipids are selected from the group consisting of phospholipids, neutral lipids and mixtures thereof.

52. The process of claim 51 wherein the phospholipids are selected to be any of a class known as phosphatidylcholines.

53. The process of claim 52 wherein the phosphatidylcholine is selected to be any fully saturated diacyl phosphatidylcholine.

54. The process of claim 53 wherein the fully saturated diacyl phosphatidylcholine is selected to be 1,2 dipalmitoyl phosphatidylcholine.

55. The process of claim 51 wherein the phospholipid is selected from the group consisting of a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, and mixtures thereof.

56. The process of claim 45 wherein the carbohydrates are selected from the group consisting of glucose, fructose, galactose, pneumogalactan, dextrose and mixtures thereof.

57. The process of claim 45 wherein the protein is selected from the group consisting of albumin and pulmonary surfactant specific proteins A, B, C, D and mixtures thereof.

58. The process of claim 45 wherein the cholesteryl ester is selected from the group consisting of cholesteryl palmitate, cholesteryl oleate, cholesteryl stearate and mixtures thereof.

59. The process of claim 45 wherein the propellants are selected to be fluorocarbons.

60. The process of claim 59 wherein the fluorocarbon is selected from the group consisting of a chlorofluorocarbon, hydrofluorocarbon and mixtures thereof.

61. The process of claim 45 wherein the propellant is selected to be carbon dioxide.

62. The process of claim 45 wherein the propellant is selected to be any pharmaceutical grade hypo-allergenic propellant in which the at least one surfactant and spreading agent are not soluble.

63. The process of claim 45 wherein 95 percent of said crystals demonstrate a particle size no greater than 4 microns in diameter.

64. A process for preparing an upper respiratory system medicament comprising:
combining at least one lipid surfactant, at least one spreading agent, at least one therapeutically active agents effective in the treatment of upper respiratory pathology and at least one propellants to form a mixture, said lipid surfactants and said spreading agents being selected from the group consisting of sterols, lipids, fatty acids, cholesteryl esters, phospholipids, carbohydrates, and proteins all in powder form, wherein said lipid surfactants, said spreading agents and said therapeutically active agents are insoluble in the propellants and said lipid surfactants are selected to be present in an amount effective in lowering surface tension of an air/liquid interface resident upon epithelial tissue lining said upper respiratory system and said spreading agents being present in an amount effective in distributing said surfactant within said interface when said propellants are evaporated from said mixture to form a mixture of lipid crystals combined with said therapeutic agents for use as the medicament.

65. The process of claim 64 wherein said lipid surfactant is selected to be present in an amount of from about 99.99 to about 50 weight percent and wherein said spreading agent is selected to be present in an amount of from about 50 to about 0.01 weight percent.

66. The process of claim 64 wherein said lipid surfactant is selected to be present in an amount of from about 80 to about 99.5 weight percent and wherein said spreading agent is selected to be present in an amount of from about 20 to about 0.5 weight percent.

67. The process of claim 64 further comprising bottling said mixture within a metered dose device.

68. The process of claim 64 wherein the sterols are selected from the group consisting of cholesterol, ergosterol, cholecalciferol and mixtures thereof.

69. The process of claim 64 wherein the fatty acids are selected from the group consisting of palmitic acid, oleic acid and mixtures thereof.

70. The process of claim 64 wherein the lipids are selected from the group consisting of phospholipids, neutral lipids and mixtures thereof.

71. The process of claim 70 wherein the phospholipids are selected to be any of a class known as phosphatidylcholines.

72. The process of claim 71 wherein the phosphatidylcholine is selected to be any fully saturated diacyl phosphatidylcholine.

73. The process of claim 72 wherein the fully saturated diacyl phosphatidylcholine is selected to be 1,2 dipalmitoyl phosphatidylcholine.

74. The process of claim 70 wherein the phospholipid is selected from the group consisting of a diacylphosphatidylglycerol, diacylphosphatidylethanolamime, diacylphosphatidylserine, diacylphosphatidylinositol, sphingomelin, Gardiolipin, lysophospholipid, plasmalogen, diether phosphonolipid, dialkyiphospholipid, and mixtures thereof.

75. The process of claim 64 wherein the carbohydrates are selected from the group consisting of glucose, fructose, galactose, pneumogalactan, dextrose and mixtures thereof.

76. The process of claim 64 wherein the protein is selected from the group consisting of albumin and pulmonary surfactant specific proteins A, B, C, D and mixtures thereof.

77. The process of claim 64 wherein the cholesteryl ester is selected from the group consisting of cholesteryl palmitate, cholesteryl oleate, cholesteryl stearate and mixtures thereof.

78. The process of claim 64 wherein said therapeutically active agent is selected from the group consisting of an anti-inflammatory, antibiotic, decongestant and gene therapy agent.

79. The process of claim 78 wherein the anti-inflammatory agent is selected to be betamethasone.

80. The process of claim 78 wherein said antibiotic is selected from the group consisting of erythromycin, amoxicillin, zythromax, Augmentin and mixtures thereof.

81. The process of claim 78 wherein the decongestant is selected to be fluorocarbons.

82. The process of claim 64 wherein the propellants are selected to be fluorocarbons.

83. The process of claim 82 wherein the fluorocarbon is selected from the group consisting of a chlorofluorocarbon, hydrofluorocarbon and mixtures thereof.

84. The process of claim 64 wherein the propellant is selected to be carbon dioxide.

85. The process of claim 64 wherein the propellant is selected to be any hyper-allergenic, pharmaceutical grade propellant in which the neither the surfactant, spreading agent or therapeutically active agent are soluble.

86. The process of claim 64 wherein 95 percent of said crystals demonstrate a particle size no greater than 4 microns in diameter.

87. A method of administering therapeutic agents, effective in the treatment of upper respiratory system pathology, directly thereto while simultaneously decreasing airflow resistance therethrough comprising administering a dose of a mixture of lipid crystals in combination with said therapeutic agents, as an aerosolized mixture of lipid crystals, through an external airway of a mammal, said mixture being comprised of at least one lipid surfactant in an amount effective in lowering surface tension of an air/liquid interface resident upon epithelial tissue lining said upper respiratory system, at least one therapeutically active agent effective in the treatment of upper respiratory system pathology and at least one propellant, said lipid surfactants being selected from the group consisting of sterols, lipids, fatty acids, cholesteryl esters, phospholipids, carbohydrates, and proteins, said surfactants and therapeutically active agents all being in powder form and insoluble in the propellants,
  whereupon, when said mixture of lipid crystals is so administered, said propellants evaporate from said mixture as said lipid crystals come into contact with, and deposit upon the epithelial lining of the upper respiratory system thereby reducing the surface tension of said air/liquid interface so as to effectively reduce the resistance to airflow therethrough while distributing said therapeutically active agent to the tissues of the upper respiratory system.

88. The method of claim 87 wherein said lipid surfactant is selected to be present in an amount of from about 99.99 to about 50 weight percent and wherein said therapeutically active agent is selected to be present in an amount of from about 50 to about 0.01 weight percent.

89. The method of claim 87 wherein said lipid surfactant is selected to be present in an amount of from about 80 to about 99.5 weight percent and wherein said therapeutically active agent is selected to be present in an amount of from about 20 to about 0.5 weight percent.

90. The method of claim 87 wherein a metered dose inhalation device is filled with said mixture of lipid crystals in combination with said therapeutically active agent and thereafter said device is utilized to administer a metered dose of said mixture through an external nasal orifice of said mammal.

91. The method of claim 87 wherein a metered dose inhalation device is filled with said mixture of lipid crystals in combination with said therapeutically active agent and thereafter said device is utilized to administer a metered dose of said mixture by means of oral inhalation.

92. The method of claim 87 wherein the sterols are selected from the group consisting of cholesterol, ergosterol, cholecalciferol and mixtures thereof.

93. The method of claim 87 wherein the fatty acids are selected from the group consisting of palmitic acid, oleic acid and mixtures thereof.

94. The method of claim 87 wherein the lipids are selected from the group consisting of phospholipids, neutral lipids and mixtures thereof.

95. The method of claim 94 wherein the phospholipids are any of a class known as phosphatidylcholines.

96. The method of claim 95 wherein the phosphatidylcholine is any fully saturated diacyl phosphatidylcholine.

97. The method of claim 96 wherein the fully saturated diacyl phosphatidylcholine is 1,2 dipalmitoyl phosphatidylcholine.

98. The method of claim 94 wherein the phospholipid is selected from the group consisting of a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, and mixtures thereof.

99. The method of claim 87 wherein the carbohydrates are selected from the group consisting of glucose, fructose, galactose, pneumogalactan, dextrose and mixtures thereof.

100. The method of claim 87 wherein the protein is selected from the group consisting of albumin and pulmonary surfactant specific proteins A, B, C, D and mixtures thereof.

101. The method of claim 87 wherein the cholesteryl ester is cholesteryl palmitate, cholesteryl oleate, cholesteryl stearate or mixture thereof.

102. The method of claim 87 wherein said therapeutically active agent is selected from the group consisting of an anti-inflammatory, antibiotic, decongestant and gene therapy agent.

103. The method of claim 102 wherein said anti-inflammatory agent is betamethasone.

104. The method of claim 102 wherein said antibioitic is selected from the group consisting of erythromycin, amoxicillin, zythromax and Augmentin.

105. The method of claim 102 wherein said decongestant is phenylephrine.

106. The method of claim 87 wherein the propellants are fluorocarbons.

107. The method of claim 106 wherein the fluorocarbon is selected from the group consisting of a chlorofluorocarbon, hydrofluorocarbon and mixtures thereof.

108. The method of claim 87 wherein the propellant is carbon dioxide.

109. The method of claim 87 wherein the propellant is selected to be any pharmaceutical grade, hypo-allergenic propellant in which neither the at least one surfactant or therapeutically active agent are soluble.

110. The method of claim 87 wherein ththeherapeutic agent is selected from the group consisting of sterols, lipids, fatty acids, cholesteryl esters, phospholipids, carbohydrates, and proteins.

111. A process for preparing an upper respiratory system medicament comprising:
  combining at least one lipid surfactant, at least one therapeutically active agent effective in the treatment of upper respiratory system pathology and at least one propellant to form a mixture, said lipid surfactants being selected from the group consisting of sterols, lipids, fatty acids, cholesteryl esters, phospholipids, carbohydrates, and proteins all in powder form, wherein said lipids and said therapeutically active agents are insoluble in the propellants and said lipids are selected to be present in an amount effective in lowering surface tension of an air/liquid interface resident upon epithelium lining said upper respiratory system and effective in distributing said therapeutic agent within said lining when said propellants are evaporated to form an aerosolized mixture of lipid crystals combined with said therapeutic agents for use as the medicament.

112. The process of claim 111 wherein said lipid surfactant is selected to be present in an amount of from about 99.99 to about 50 weight percent and wherein said therapeutically active agent is selected to be present in an amount of from about 50 to about 0.01 weight percent.

113. The process of claim 111 wherein said lipid surfactant is selected to be present in an amount of from about 80 to about 99.5 weight percent and wherein said therapeutically active agent is selected to be present in an amount of from about 20 to about 0.5 weight percent.

114. The process of claim 111 further comprising bottling said mixture within a metered dose administration device.

115. The process of claim 111 wherein the sterols are selected from the group consisting of cholesterol, ergosterol, cholecalciferol and mixtures thereof.

116. The process of claim 111 wherein the fatty acids are selected from the group consisting of palmitic acid, oleic acid and mixtures thereof.

117. The process of claim 111 wherein the lipids are selected from the group consisting of phospholipids, neutral lipids and mixtures thereof.

118. The process of claim 117 wherein the phospholipids are any of a class known as phosphatidylcholines.

119. The process of claim 118 wherein the phosphatidylcholine is any fully saturated diacyl phosphatidylcholine.

120. The process of claim 119 wherein the fully saturated diacyl phosphatidylcholine is 1,2 dipalmitoyl phosphatidylcholine.

121. The process of claim 117 wherein the phospholipid is selected from the group consisting of a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, and mixtures thereof.

122. The process of claim 111 wherein the carbohydrates are selected from the group consisting of glucose, fructose, galactose, pneumogalactan, dextrose and mixtures thereof.

123. The process of claim 111 wherein the protein is selected from the group consisting of albumin and pulmonary surfactant specific proteins A, B, C, D and mixtures thereof.

124. The process of claim 111 wherein the cholesteryl ester is selected from the group consisting of cholesteryl palmitate, cholesteryl oleate, cholesteryl stearate and mixtures thereof.

125. The process of claim 111 wherein said therapeutically active agent is selected from the group consisting of an anti-inflammatory, antibiotic, decongestant and therapy agent.

126. The process of claim 125 wherein said anti-inflammatory agent is betamethasone.

127. The process of claim 125 wherein said antibioitic is selected from the group consisting of erythromycin, amoxicillin, zythromax and Augmentin.

128. The process of claim 125 wherein said decongestant is phenylephrine.

129. The process of claim 111 wherein the therapeutically active agent is selected from the group consisting of sterols, lipids, fatty acids, cholesteryl esters, phospholipids, carbohydrates, and proteins.

130. The process of claim 111 wherein the propellants are fluorocarbons.

131. The process of claim 130 wherein the fluorocarbon is selected from the group consisting of a chlorofluorocarbon, hydrofluorocarbon and mixtures thereof.

132. The process of claim 111 wherein the propellant is selected to be carbon dioxide.

133. The process of claim 111 wherein the propellant is selected to be any pharmaceutical grade, hypo-allergenic propellant in which neither the at least one surfactant or therapeutic agent are not soluble.

* * * * *